(12) United States Patent
Asakawa et al.

(10) Patent No.: US 7,199,152 B2
(45) Date of Patent: Apr. 3, 2007

(54) TNF-α PRODUCTION INHIBITOR COMPRISING KAVALACTONE AS AN ACTIVE INGREDIENT

(75) Inventors: Yoshinori Asakawa, Tokushima (JP); Sachiko Okabe, Ageo (JP); Masashi Yamada, Sumida-ku (JP); Yukie Suma, Sumida-ku (JP); Hiroto Suzuki, Sumida-ku (JP); Masayuki Uchida, Odawara (JP); Natsuko Murata, Odawara (JP)

(73) Assignee: Meiji Dairies Corporation, Tokyo (JP)

( * ) Notice: Subject to any disclaimer, the term of this patent is extended or adjusted under 35 U.S.C. 154(b) by 159 days.

(21) Appl. No.: 10/185,045

(22) Filed: Jul. 1, 2002

(65) Prior Publication Data

US 2002/0173540 A1 Nov. 21, 2002

Related U.S. Application Data

(63) Continuation of application No. 09/941,713, filed on Aug. 30, 2001, now Pat. No. 6,608,105.

(30) Foreign Application Priority Data

Dec. 18, 2000 (JP) ............................. 2000-383095

(51) Int. Cl.
*A61K 31/35* (2006.01)
*A61K 31/70* (2006.01)
*A61K 39/395* (2006.01)

(52) U.S. Cl. ........................ 514/460; 514/456; 514/25; 514/27; 424/195.1

(58) Field of Classification Search ................. 514/460, 514/456, 25, 27; 424/195.1
See application file for complete search history.

(56) References Cited

U.S. PATENT DOCUMENTS

| 5,296,224 A | | 3/1994 | Schwabe | |
|---|---|---|---|---|
| 5,977,120 A | * | 11/1999 | Giles, Jr. | ............... 214/263.31 |
| 5,981,496 A | * | 11/1999 | Cohen et al. | ................. 514/25 |
| 6,025,363 A | * | 2/2000 | Giles, Jr. | ............... 514/263.31 |
| 6,143,300 A | * | 11/2000 | Stevenot | ...................... 424/734 |
| 6,288,109 B1 | | 9/2001 | Chatterjee et al. | |
| 2001/0031783 A1 | * | 10/2001 | Steiner | ........................ 514/460 |
| 2002/0077351 A1 | | 6/2002 | Asakawa et al. | |
| 2002/0173540 A1 | | 11/2002 | Asakawa et al. | |

FOREIGN PATENT DOCUMENTS

| DE | 19716 660 | 10/1998 |
|---|---|---|
| EP | 0 523 591 A2 | 1/1993 |
| EP | 0 664 131 | 7/1995 |
| GB | 1 214 936 | 12/1970 |
| JP | 5-502457 | 4/1993 |

OTHER PUBLICATIONS

Fujiki et al., Dietary factors, Cancer detection and prevention online, 200(Jan.-Feb.), vol. 24(supp)/1, Google database.*
Fujiki, Hirota, Two stages of Cancer prevention with green tea, J Cancer Res Cli Oncol, 1999, vol. 125, pp. 589-597.*
H.J. Meyer, "Antagonistische Wirkungen Geniuner Kawa-Pyrone Bei Experimentellen Entzuendungen Und Fieber", Klin. Wschr., vol. 43, No. 8, 1965, pp. 469-470, XP-001083832 (w/English Summary).
Archives of Disease in Childhood, vol. 66, pp. 561-562, 1991.
B. Beutler, et al., Nature, vol. 316, pp. 552-551, "Identity of Tumour Necrosis Factor and the Macrophage-Secreted Factor Cachectin", Aug. 8, 1985.
B. Beutler, et al., Science, vol. 229, pp. 869-871, "Passive Immunization Against Cachectin/Tumor Necrosis Factor Protects Mice from Lethal Effect of Endotoxin", Aug. 30, 1985.
G. Boonen, et al., Planta Medica, vol. 64, pp. 504-506, "Influence of Genuine Kavapyrone Enantiomers on the GABAA Binding Site", 1998.
G. Boonen, et al., Planta Medeca, vol. 64, pp. 507-510, "In Vivo Effects of the Kavapyrones (+)- Dihydromethysticine and (±) -Kavain on Dopamine, 3,4-Dihydroxyphenylacetic Acid Serotonin and 5-Hydroxyindoleacetic Acid Levels in Striatal and Coritcal Brain Regions", 1998.
B.J. Dezube, et al., Journal of Acquired Immune Deficiency Syndromes, vol. 5, No. 11, pp. 1099-1104, Cytokine Dysregulation in Aids: In Vivo Overexpression of MRNA of Tumor Necrosis Factor-Alpha and its Correlation with that of the Inflammatory Cytokine Gro, 1992.
M.J. Elliott, et al., The Lancet, vol. 344, pp. 1105-1110, "Randomised Double-Blind Comparison of Chimeric Monoclonal Antibody to Tumour Necrosis Factor Alpha (CA2) Versus Placebo in Rheumatoid Arthritis", Oct. 22, 1994.
M.J. Elliott, et al., The Lancet, vol. 344, p. 1125-1127, "Repeated Therapy with Monoclonal Antibody to Tumour Necrosis Factor Alpha (CA2) in Patients with Rheumatoid Arthritis", Oct. 22, 1994.
H. Fujiki, et al., Proceedings of the Fifty-Eigth Annual Meeting of the Japanese Cancer Association, S11-3, vol. 90, "Cancer Prevention with Drinking Green Tea", Sep. 29 to Oct. 1, 1999.
G.E. Grau, et al., Science, vol. 237, pp. 1210-1212, "Tumour Necrosis Factor (Cachectin) as an Essential Mediator in Murine Cerebral Malaria", Sep. 4, 1987.

(Continued)

*Primary Examiner*—Vickie Kim
(74) *Attorney, Agent, or Firm*—Oblon, Spivak, McClelland, Maier & Neustadt, P.C.

(57) ABSTRACT

The present invention provides a TNF-α production inhibitor containing a kavalactone as an active ingredient, which inhibitor has high safety, exerts an excellent effect of inhibiting TNF-α production, and is useful as a drug or an animal drug for preventing, ameliorating, or treating diseases such as cachexia attributed to cancer or infectious diseases, chronic rheumatoid arthritis, inflammatory diseases, osteoarthritis, systemic lupus erythematosus (SLE), rejection during bone marrow transplantation, multiple organ failure, AIDS, meningitis, hepatitis, and type-II diabetes. The present invention also provides a preventive, ameliorating, or therapeutic agent for diseases caused by abnormal production of TNF-α, the agent containing a kavalactone as an active ingredient.

3 Claims, 1 Drawing Sheet

OTHER PUBLICATIONS

G.S. Hotamisligil, et al., Science, vol. 259, pp. 87-90, Adipose Expression of Tumour Necrosis Factor-Alpha: Direct Role in Obesity-Linked Insulin Resistance, Jan. 1, 1993.

K. Kanno, Kanzo, vol. 33, pp. 213-217, "Clinical Research on Serum TNF-Alpha in Acute Hepatic Disorders", Sep. 11, 1991.

T. Matsubara, et al., Clinical Immunology and Immunopathology, vol. 56, pp. 29-36, "Serum Levels of Tumor Necrosis Factor, Interleukin 2 Receptor, and Interferon-Gamma in Kawasaki Disease Involved Coronary-Artery Lesions", 1990.

C.P.J. Maury, et al., Arthritis and Rheumatism, vol. 32, No. 2, pp. 146-150, "Tumor Necrosis Factor in the Serum of Patients with Systemic Lupus Erythematosus", Feb. 1989.

F.P. Nestel, et al., J. Exp. Med., vol. 175, pp. 405-413, "Macrophage Priming and Lipoplysaccharade-Triggered Release of Tumor Necrosis Factor Alpha During Graft-Versus-Host Disease", Feb. 1992.

E.C.C. Rankin, et al., British Journal of Rheumatology, vol. 34, pp. 334-342, "The Therapeutic Effects of An Engineered Human Anti-Tumor Necrosis Factor Alpha Antibody (CDP571) in Rheumatoid Arthritis", 1995.

Rinsbroi, vol. 17, No. 10, pp. 2006-2008, "TNF and LT", 1991.

M.K. Sharief, et al., The New England Journal of Medicine, vol. 325, No. 7, pp. 467-472, "Association Between Tumor Necrosis Factor-Alpha and Disease Progression in Patients with Multiple Sclerosis", Aug. 15, 1991.

S. Sotheeswaran, Chemistry in Australia, pp. 377-378, Kawa and the Australian Aborigine, Oct. 1987.

H.F. Starnes, Jr., The Journal of Immunology, vol. 145, No. 12, pp. 4185-4191, "Anti-IL-6 Monoclonal Antibodies Protect Against Lethal *Escherichia coli* Infection and Lethal Tumor Necrosis Factor-Alpha Challenge in Mice", Dec. 15, 1990.

C. Tetta, et al., Annals of the Rheumatic Diseases, vol. 49, pp. 665-667, "Tumor Necrosis Factor in Serum and Synovial Fluid of Patients with Active and Severe Rheumatoid Arthritis", 1990.

The Journal of Rheumatology, vol. 17, pp. 1107-1108, 1990.

G. Venn, et al., Arthritis and Rheumatism, vol. 36, No. 6, pp. 819-826, "Elevated Synovial Fluid Levels of Interleukin-6 and Tumor Necrosis Factor Associated with Early Experimental canine Osteoarthritis", Jun. 1993.

A. Waage, et al., The Lancer, vol. 1, pp. 355-357, "Association Between Tumour Necrosis Factor in Serum and Fatal Outcome in Patients with Meningococcal Disease", Feb. 14, 1987.

* cited by examiner

** : p<0.01 (Aspin-Welch test)
\# : p<0.5 (Student's *t* test)

TNF-α PRODUCTION INHIBITOR COMPRISING KAVALACTONE AS AN ACTIVE INGREDIENT

BACKGROUND OF THE INVENTION

1. Field of the Invention

The present invention relates to a TNF-α production inhibitor containing a kavalactone as an active ingredient, and to a preventive, ameliorating, or therapeutic agent for diseases caused by abnormal production of TNF-α.

2. Background Art

TNF (Tumor Necrosis Factor) was discovered as an antitumor cytokine, and has been elucidated to have carcinostatic activity (i.e., the effect of inhibiting cancer cell growth or necrotizing cancer cells), and to participate in a series of inflammatory responses or immunoreactions, as well as in differentiation or maturation of cells.

Recent studies have shown that excessive production of TNF-α induces onset of a variety of diseases, including cachexia attributed to cancer or infectious diseases (*Nature*, 316: 552, 1985), septic shock (*J. Immunol.*, 145: 4185, 1990; *Science*, 229: 869, 1985; *Shock*, 30: 1990), chronic rheumatoid arthritis (*Ann. Rheum. Dis.*, 49: 665, 1990; *Lancet*, 344: 1105, 1994; *Lancet*, 344: 1125, 1994; *British J. Rheum.*, 34: 334, 1995), inflammatory diseases such as ulcerative colitis and Crohn disease (*Arch. Dis. Child*, 66: 561, 1991; *Gastroenterology*), osteoarthritis (*Arthritis Rheum.*, 36: 819, 1993), Kawasaki's disease (*Clin. Immunol. Immunopathol.*, 56: 29, 1990), multiple sclerosis (*N. Engl. J. Med.*, 325(7): 467, 1991), Behchet's disease (*J. Rheumatol.*, 17: 1107, 1990), systemic lupus erythematosus (STE) (*Arthritis Rheum.*, 32: 146, 1989), rejection during bone marrow transplantation (*J. Exp. Med.*, 175: 405, 1992), multiple organ failure (*Rinshoi*, 17(20), 2006, 1991), malaria (*Science*, 237: 1210, 1987), AIDS (*J. Acquir. Immune Defic. Syndr.*, 5: 1099, 1992), meningitis (*Lancet*, 1: 355, 1987), hepatitis (*Kozo Kanno, Kanzo*, 33: 213, 1992), and type-II diabetes (*Science*, 259: 87, 1993).

The aforementioned diseases caused by excessive production of TNF-α have hitherto been treated from a mere palliative approach by use of steroid agents, anti-inflammatory agents, antibiotics, etc., and drugs for fundamentally treating the diseases have not yet been developed.

Kava is a plant found in Fiji and belongs to *Piperaceae, Piper L.* (nomenclature: *Piper Methysticum Forst.*, alias: *Yangona*). Since anesthetic beverages are obtained from the kava root, in Oceania, kava is widely cultivated by privileged people and is used in traditional ceremonies or events (*Chem. Australia.* Oct 377–378 (1987)).

It has been reported that an extract obtained from the dried kava root through extraction with water contains a class of α-pyrone derivatives called kavalactones which induce numbness of the lips or tongue or exert sedative effect, such as methysticin (*Chem. Australia.* Oct 377–378 (1987), *Planta Med.* 64 504–506 (1998)).

Studies performed In the University of New South Wales have elucidated that kavalactones exert a sedative effect through a mechanism different from those of other sedative drugs which exert sedative effects when being bound to receptors present in the brain (*Planta Med.* 65 507–510 (1998)). It has also been reported that kavalactones exert an analgesic effect in a manner different from that of a formulated analgesic drug such as aspirin, and that, unlike morphine, kavalactones are not bound to receptors in the brain (e.g., European Patent Application Laid-Open Nos. 664131 and 523591, and Japanese Kohyo (PCT) Patent Publication No. 5-502457).

It has also been reported that kava extract exerts an antibacterial effect and is useful for treating Helicobacter pylori infection (German Patent Application Laid-Open No. 19716660), and that the kava extract exerts a neuroprotective effect and is useful for treating brain dysfunction, Alzheimer's disease, brain injury, etc. (e.g., European Patent Application Laid-Open No. 523591, and Japanese Kohyo (PCT) Patent Publication No. 5-502457).

However, until the present invention was attained, kavalactones and kava extract have not been known to exert the effect of inhibiting TNF-α production.

SUMMARY OF THE INVENTION

In view of the foregoing, the present inventors have performed studies on naturally occurring substances which inhibit production of TNF-α, and have found that kavalactones contained in kava extract exert an excellent effect of inhibiting TNF-α production, and that the kavalactones are useful as TNF-α production inhibitors and as preventive, ameliorating, or therapeutic agents for a variety of diseases caused by abnormal production of TNF-α. The present invention has been accomplished on the basis of this finding.

Thus, an object of the present invention is to provide a drug which is endowed with high safety, inhibits TNF-α production, and is useful as a preventive or therapeutic agent for the aforementioned diseases.

Accordingly, the present invention provides a TNF-α production inhibitor comprising a kavalactone as an active ingredient.

The present invention also provides a preventive, ameliorating, or therapeutic agent comprising a kavalactone as an active ingredient for diseases caused by abnormal production of TNF-α.

The present invention further provides a method for the treatment of diseases caused by abnormal production of TNF-α, which method comprises administering an effective amount of a kavalactone.

The present invention further provides use of a kavalactone for the manufacture of a TNF-α production inhibitor.

Still, the present invention provides use of a kavalactone for the manufacture of a medicament for preventing, ameliorating, or treating diseases caused by abnormal production of TNF-α.

Preferably, the kavalactone is one or more species selected from the group consisting of desmethoxyyangonin, dihydrokavain, kavain, yangonin, methysticin, dihydromethysticin, and 7,8-epoxyyangonin.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with accompanying drawings, in which.

DETAILED DESCRIPTION OF PREFERRED EMBODIMENTS

Figure 1:
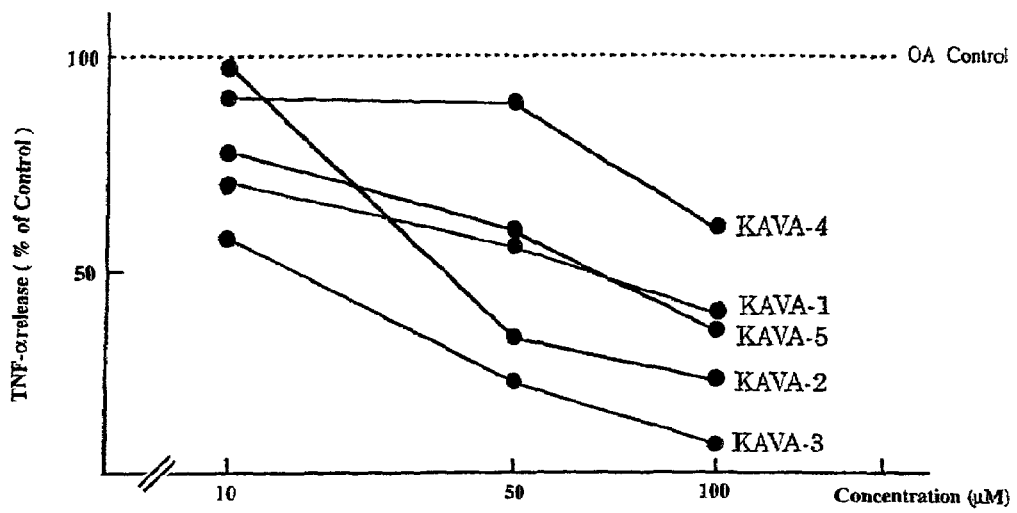
FIG. 1 shows a graph indicating inhibitory effects of KAVA-1, KAVA-2, KAVA-3, KAVA-4, and KAVA-5 on TNF-α production in BALB/3T3 cells stimulated by okadaic acid.

Kavalactone contained, as an active ingredient, in the TNF-α production inhibitor of the present invention refers to a class of α-pyrone derivatives contained in the root of kava (*Piper Methysticum G. Forst*) which belongs to *Piperaceae, Piper L.* Specific examples of the α-pyrone derivatives include desmethoxyyangonin, dihydrokavain, kavain, yangonin, methysticin, dihydromethysticin, and 7,8-epoxyyangonin, which are represented by the following formulas.

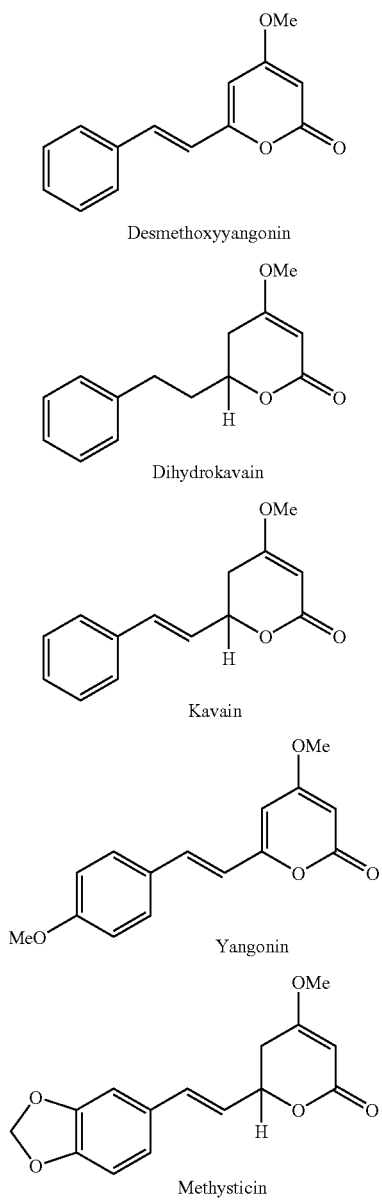

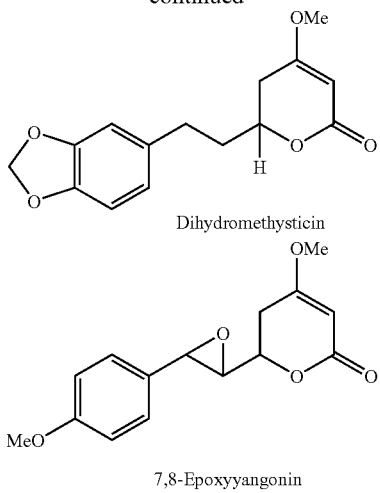

These α-pyrone derivatives have a variety of isomers, including geometrical isomers such as cis-isomers and trans-isomers, optical isomers such as d-isomers and l-isomers, and rotational isomers. In the present invention, any of such isomers can be used, so long as the isomer can exert the effect of inhibiting TNF-α production. In the present invention, these pyrone derivatives also include racemic modifications and a mixture of diastereomers.

From the viewpoint of the effect of inhibiting TNF-α production, examples of particularly preferred kavalactones include desmethoxyyangonin (KAVA-3: compound 1), (+)-dihydrokavain (KAVA-4: compound 2), (+)-kavain (KAVA-5: compound 3), yangonin (KAVA-2: compound 4), (+)-methysticin (KAVA-1: compound 5), (+)-dihydromethysticin (KAVA-6: compound 6), and 7,8-epoxyyangonin (compound 7).

These α-pyrone derivatives may be used singly or in combination of two or more species as kavalactone employed in the TNF-α production inhibitor of the present invention.

Kavalactones used in the present invention may be obtained from the kava root by means of a known extraction method, or obtained through synthesis by means of a published method (*Acta Chemica Scandinavica B* 30, 7: 613–678, 1976; *Planta Med.*, 64: 504, 1998).

In the case in which kavalactones are obtained through extraction, the aforementioned kavalactones separated from kava extract and purified can be used. However, an extraction fraction containing a plurality of compounds may also be used, so long as the fraction exhibits the effect of inhibiting TNF-α production.

Since the thus-obtained kavalactones exert an excellent effect of inhibiting TNF-α production in vivo and in vitro as described below in Examples, the kavalactones can be used as a TNF-α production inhibitor for mammals including humans, and as a preventive, ameliorating, or therapeutic agent for a variety of diseases caused by abnormal production of TNF-α, including cachexia attributed to cancer or infectious diseases, septic shock, chronic rheumatoid arthritis, inflammatory diseases such as ulcerative colitis and Crohn disease, osteoarthritis, Kawasaki's disease, multiple sclerosis, Behchet's disease, systemic lupus erythematosus (SLE), rejection during bone marrow transplantation, multiple organ failure, malaria, AIDS, meningitis, hepatitis, and type-II diabetes.

When the kavalactone according to the present invention is administered as a drug, the amount and frequency of administration vary with pathological conditions, age, weight, manner of administration, and other conditions. In the case of peroral administration, the daily dose is typically 0.1–1,000 mg for adults, but the daily dose varies with pathological conditions and other conditions (e.g., 10–500 mg or 30–300 mg). Regarding the case in which pure kavalactone is employed, a daily dose of 200 mg has been reported (Kretschmer "Kavain als Psychopharmkon," NMW 4/1970, 154–158).

When the kavalactone according to the present invention is used as a TNF-α production inhibitor and as a preventive, ameliorating, or therapeutic agent for diseases caused by abnormal production of TNF-α, the kavalactone is prepared in the form of a typical pharmaceutical product. For example, the kavalactone is formulated in a form suitable for oral administration or parenteral administration (e.g., intraarticular administration or enteric administration), such as a pharmaceutical composition obtained by mixing the drug of the present invention with a pharmaceutically acceptable carrier (e.g., an excipient, a binder, a disintegrant, a sweetening agent, a flavoring agent, an emulsifying agent, a diluent, or a dissolution promoter) and processing to have a product form of, for example, tablet, pill, powder, granule, capsule, troche, syrup, solution, emulsion, suspension, or injection.

Examples of excipients include lactose, cornstarch sucrose, glucose, sorbitol, and crystalline cellulose. Examples of binders include polyvinyl alcohol, polyvinyl ether, ethyl cellulose, methyl cellulose, gum arabi, tragacanth, gelatin, shellac, hydroxypropyl cellulose, hydroxypropyl starch, and polyvinyl pyrrolidone.

Examples of disintegrants include starch, agar, gelatin powder, crystalline cellulose, calcium carbonate, sodium hydrogencarbonate, calcium citrate, dextran, and pectin. Examples of lubricants include magnesium stearate, talc, polyethylene glycol, silica, and hydrogenated vegetable oil. Any pharmaceutically acceptable coloring agent may be used. Examples of sweetening and flavoring agents include cocoa powder, menthol, aromatic acids, peppermint oil, borneol, and cinnamon powder. If necessary, tablets or granules may optionally be subjected to sugar coating, gelatin coating, or similar coating.

In the case of preparation of injections, if necessary, a pH-regulating agent, a buffer, a stabilizer, or a preservative is added to the injections, to thereby prepare agents for subcutaneous injection, intramuscular injection, or intravenous injection, by means of a customary method. Injection preparations may be stored in a container and freeze-dried, to thereby provide solid products, and the solid products may be prepared into injections upon use. A single dose of the injection may be stored in a container, or a plurality of doses may be stored in a single container.

EXAMPLES

The present invention will next be described in more detail by way of examples, which should not be construed as limiting the invention thereto.

Example 1

Isolation of Components Having a TNF-α Release Inhibitory Effect through Extraction Dried kava root (1.0 kg) was subjected to extraction by use of methanol for 16 days. The resultant mixture was subjected to filtration under reduced pressure, and the filtrate was concentrated under reduced pressure, to thereby yield a residue (152.0 g). The entirety of the residue was partitioned by use of water and ethyl acetate (AcOEt), and the resultant ethyl acetate phase was concentrated under reduced pressure, to thereby yield an ethyl acetate extract (76.17 g). The entirety of the extract was added to a silica gel column (product of Merck, 1 kg (70–230 mesh 500 g+230–400 mesh 500 g)) for chromatography by use of n-hexane/ethyl acetate. In the course of chromatography, the ethyl acetate concentration of the solvent was gradually elevated so as to effect elution/extraction in the following concentration profile: n-hexane (500 ml); 5% ethyl acetate/n-hexane (500 ml); 10% ethyl acetate/n-hexane (500 ml); 15% ethyl acetate/n-hexane (500 ml); 20% ethyl acetate/n-hexane (500 ml); 25% ethyl acetate/n-hexane (500 ml); 30% ethyl acetate/n-hexane (500 ml); 35% ethyl acetate/n-hexane (500 ml); 40% ethyl acetate/n-hexane (500 ml); 45% ethyl acetate/n-hexane (500 ml); 50% ethyl acetate/n-hexane (500 ml); 60% ethyl acetate/n-hexane (500 ml); 70% ethyl acetate/n-hexane (500 ml); 80% ethyl acetate/n-hexane (500 ml); 85% ethyl acetate/n-hexane (500 ml); 90% ethyl acetate/n-hexane (500 ml); and ethyl acetate (500 ml). Collection of fractions was initiated from the eluate corresponding to 20% ethyl acetate/n-hexane, with the volume of each fraction being 20 ml. The eluate corresponding to fractions 65 to 74 was concentrated under reduced pressure, to thereby yield 1.48 g of crude crystals. The crystals were recrystallized from ethyl acetate/n-hexane, to thereby yield 1.218 g of compound 1: 5,6-dehydrokavain, as pale yellow needles. In a similar manner, crude crystals (3.78 g) obtained from the eluate corresponding to fractions 75 to 82 were recrystallized from ethyl acetate/n-hexane, to thereby yield 3.513 g of compound 2: dihydrokavain, as colorless needles. Crude crystals (5.36 g) obtained from the eluate corresponding to fractions 86 to 94 were recrystallized from ethyl acetate/ether, to thereby yield 4.744 g of compound 3: kavain, as colorless prisms. Crude crystals (1.27 g) obtained from the eluate corresponding to fractions 97 to 102 were recrystallized from ethyl acetate/ether, to thereby yield 0.847 g of compound 4: yangonin, as pale yellow prisms. The eluent corresponding to fractions 103 to 115 was concentrated under reduced pressure, to thereby yield a residue (8.21 g). The residue was subjected to chromatography by use of a silica gel column (product of Merck, 300 g (70–230 mesh 150 g+230–400 mesh 150 g)) and chloroform/ether solvent. In the course of chromatography, the ether concentration was gradually elevated. From the eluent corresponding to 25% ether/chloroform, 1.322 g of compound 4: yangonin was obtained. Subsequently, crude crystals obtained from the eluent corresponding to 30% ether/chloroform was recrystallized from ethyl acetate/ether, to thereby yield 5.661 g of compound 5: methysticin, as colorless needles. A residue (385 mg) obtained from the eluent corresponding to fractions 138 to 142 was placed on a Sephadex LH-20 column (product of Pharmacia, 30 g), and chromatography was performed by use of chloroform/methanol (1:1) solvent for development. Twenty mL of the eluent was collected per fraction (Fr.). From the eluent corresponding to fractions 5 to 7, 59 mg of pale yellow-white novel compound 7: 7,8-epoxyyangonin was obtained.

Compound 1 (KAVA-3) 5,6-Dehydrokavain (Desmethoxyyangonin); (4-methoxy-6-(2-phenylvinyl-2H-pyran-2-one):

m.p. 138–140° C., pale yellow needles EI-MS: m/z 228 (M+, 100%), 211 (10%), 200 (36%), 185 (15%), 157 (27%) HR-MS: m/z 228.0763, $C_{14}H_{12}O_3$ requires 228.0787, FT-IR (KBr) $v_{max}$ cm$^{-1}$: 3081, 1721 (C=O), 1644 (C=C), 1611, 1557, 1256, 1154, UV (EtOH) $\lambda_{max}$ nm (log $\epsilon$): 344.5 (4.32), 255 (4.05), 231.5 (4.15), 225 (4.14), 209 (4.28) 600 MHz $^1$H NMR (CDCl$_3$): δ 3.82 (3H, s, 4-OMe), 5.50 (1H, d, J=2.2 Hz, H-3), 5.95 (1H, d, J=2.2 Hz, H-5), 6.58 (1H, d, J=16.2 Hz, H-7), 7.33 (1H, br. t, J=7.1 Hz, 4'-H), 7.38 (2H, br. t, J=7.1 Hz, 3', 5'-H), 7.49 (2H, br. d, J=7.1 Hz, 2', 6'-H), 7.50 (1H, d, J=16.2 Hz, H-8). 150 MHz $^{13}$C NMR (CDCl$_3$): δ 55.9 (q, 4-OMe), 88.8 (d, C-3), 101.3 (d, C-5), 118.6 (d, C-7), 127.4 (d, C-2' and C-6'), 128.9 (d, C-3' and C-5'), 129.4 (d, C-4'), 135.2 (s, C-1'), 135.7 (d, C-8), 158.6 (s, C-6), 164.0 (s, C-2), 171.0 (s, C-4).

The structural formula thereof is shown below.

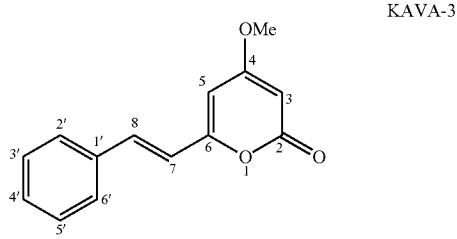

KAVA-3

Compound 2 (KAVA-4) (+)-Dihydrokavain; (4-methoxy-2-(2-phenylvinyl)-2H,3H-oxin-2-one m.p. 57–60° C., colorless needles [α]$_D^{20}$+45.7° (c0.50, CHCl$_3$) EI-MS: m/z 232 (M+, 61%), 200 (30%), 173 (15%), 141 (26%), 127 (100%) HR-MS: m/z 232.1094, $C_{14}H_{16}O_3$ requires 232.1100 FT-IR (KBr) $v_{max}$ cm$^{-1}$: 1707 (C=O), 1624, 1225, 1090, 1038 UV (EtOH) $\lambda_{max}$ nm (log $\epsilon$): 233.0 (4.01), 207.0 (4.08)

600 MHz $^1$H NMR (CDCl$_3$): δ 1.93 (1H, m, H-7), 2.13 (1H, m, H-7), 2.30 (1H, dd, J=3.8, 17.0 Hz, H-5), 2.50 (1H, ddd, J=1.6, 11.8, 17.0 Hz, H-5), 2.79 (1H, m, H-8), 2.88 (1H, m, H-8), 3.72 (3H, s, 4-OMe), 4.36 (1H, m, H-6), 5.14 (1H, d, J=1.6 Hz, H-3), 7.20 (1H, br. t, J=7.1 Hz, 4'-H), 7.21 (2H, br. d, J=7.1 Hz, 2', 6'-H), 7.49 (2H, br. t, J=7.1 Hz, 3', 5'-H). 150 MHz $^{13}$C NMR (CDCl$_3$): δ 30.9 (t, C-8), 33.0 (t, C-5), 36.3 (t, C-7), 55.9 (q, 4-OMe), 74.7 (d, C-6), 90.3 (d, C-3), 126.1 (d, C-4'), 128.4 (d, C-2' and C-6'), 128.5 (d, C-3' and C-5'), 140.8 (s, C-1'), 167.2 (s, C-2), 172.7 (s, C-4).

The structural formula thereof is shown below.

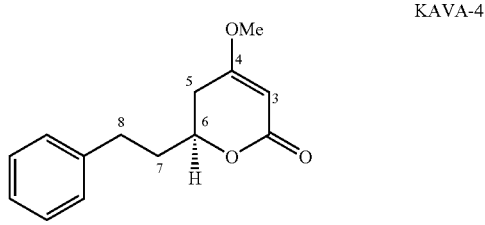

KAVA-4

Compound 3 (KAVA-5) (+)-Kavain; (4-methoxy-2-(2-phenylvinyl)-2H,3H-oxin-2-one)

m.p. 106–108° C., colorless needles [α]$_D^{20}$+116.3° (c1.01, CHCl$_3$) EI-MS: m/z 230 (M+, 27%), 202 (43%), 186 (13%), 128 (31%), 98 (100%) HR-MS: m/z 230.0951, $C_{14}H_{14}O_3$ requires 230.0943 FT-IR (KBr) $v_{max}$ cm$^{-1}$: 1703 (C=O), 1626, 1248, 1231 UV (EtOH) $\lambda_{max}$ nm (log $\epsilon$): 244.5 (4.41), 205.0 (4.48) 600 MHz $^1$H NMR (CDCl$_3$): δ 2.54 (1H, dd, J=4.4, 17.0 Hz, H-5), 2.66 (1H, ddd, J=1.4, 11.0, 17.0 Hz, H-5), 3.76 (3H, S, 4-OMe), 5.05 (1H, ddd, J=4.4, 6.3, 11.0 Hz, H-6), 5.19 (1H, d, J=1.4 Hz, H-3), 6.26 (1H, dd, J=6.3, 15.9 Hz, H-7), 6.73 (1H, br, d, J=15.9 Hz, H-8), 7.27 (1H, br. t, J=7.1 Hz, 4'-H), 7.33 (2H, br. t, J=7.1 Hz, 3', 5'-H), 7.39 (2H, br. d, J=7.1 Hz, 2', 6'-H). 150 MHz 13C NMR (CDCl$_3$): δ 33.2 (t, C-5), 56.0 (q, 4-OMe), 75.8 (d, C-6), 90.4 (d, C-3), 125.4 (d, C-7), 126.6 (d, C-2' and C-6'), 128.2 (d, C-4'), 128.6 (d, C-3' and C-5'), 133.0 (d, C-8), 135.7 (s, C-1'), 166.6 (s, C-2), 172.2 (s, C-4).

The structural formula thereof is shown below.

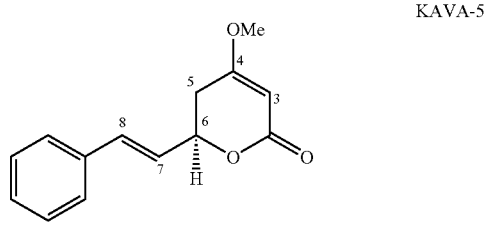

KAVA-5

Compound 4 (KAVA-2) Yangonin; (4-methoxy-6-(2-(4-methoxyphenyl)vinyl)-2H-pyran-2-one)

m.p. 153–155° C., yellow needles EI-MS: m/z 258 (M+, 100%), 230 (38%), 215 (13%), 187 (33%) HR-MS: m/z 258.0896, $C_{15}H_{14}O_4$ requires 258.0892 FT-IR (KBr) $v_{max}$ cm$^{-1}$: 1717 (C=O), 1644 (C=C), 1603, 1555, 1256, 1154 UV (EtOH) $\lambda_{max}$ nm (log $\epsilon$): 357.5 (4.42), 260.0 (3.89), 218.0 (4.28) 600 MHz $^1$H NMR (CDCl$_3$): δ 3.81 (3H, s, 4'-OMe), 3.82 (3H, s, 4-OMe), 5.47 (1H, d, J=2.2 Hz, H-3), 5.89 (1H, d, J=2.2 Hz, H-5), 6.44 (1H, d, J=15.7 Hz, H-7), 6.90 (2H, d, J=8.8 Hz, 3', 5'-H), 7.44 (2H, d, J=8.8 Hz, 2', 6'-H), 7.45 (1H, d, J=15.7 Hz, H-8). 150 MHz $^{13}$C NMR (CDCl$_3$): δ 55.3 (q, 4'-OMe), 55.8 (q, 4-OMe), 88.3 (d, C-3), 100.4 (d, C-5), 114.3 (d, C-3' and C-5'), 116.3 (d, C-7), 127.9 (s, C-1'), 128.9 (d, C-2' and C-6'), 135.4 (d, C-8), 159.0 (s, C-6), 160.7 (s, C-4'), 164.1 (s, C-2), 171.2 (s, C-4).

The structural formula thereof is shown below.

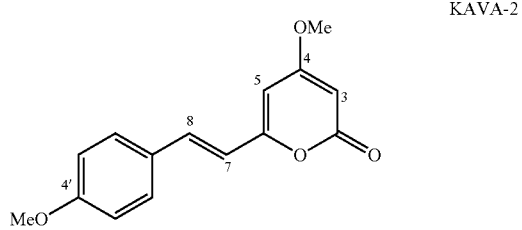

KAVA-2

Compound 5 (KAVA-1) (+)-Methysticin; (2-(2-benzo[3,4-d]1,3-dioxolan-5-ylvinyl-4-methoxy-2H,3H,-oxin-2-one)

m.p. 139–141° C., colorless needles [α]$_D^{20}$+115.9° (c0.50, CHCl$_3$) EI-MS: m/z 274 (M+, 100%), 246 (10%), 175 (19%), 148 (81%), 135 (82%) HR-MS: m/z 274.0833, $C_{15}H_{14}O_5$ requires 274.0841 FT-IR (KBr) $v_{max}$ cm$^{-1}$: 1711 (C=O), 1628, 1252, 1217, 1038 UV (EtOH) $\lambda_{max}$ nm (log $\epsilon$): 305.5 (3.89), 264.5 (4.13), 225.5 (4.38), 207.0 (4.44) 600 MHz $^1$H NMR (CDCl$_3$): δ 2.53 (1H, dd, J=4.4, 17.0 Hz, H-5), 2.65 (1H, ddd, J=1.4, 11.0, 17.0 Hz, H-5), 3.77 (3H, s, 4-OMe), 5.02 (1H, ddd, J=4.4, 6.6, 11.0 Hz, H.-6), 5.19 (1H, d, J=1.4 Hz, H-3), 6.07 (2H, s, —O—CH$_2$—O—), 6.09 (1H, dd. J=6.6, 15.9 Hz, H-7), 6.64 (1H, br. d, J=15.9 Hz, H-8), 6.76 (1H, d, J=8.0 Hz, 5'-H), 6.83 (1H, dd, J=1.9, 8.8 Hz, 6'-H), 6.92 (1H, d, J=1.9 Hz, 2'-H). 150 MHz 13C NMR (CDCl$_3$) δ 33.3 (t, C-5), 56.1 (q, 4-OMe), 76.0 (d, C-6), 90.5 (d, C-3), 101.2 (t, —O—CH$_2$—O—), 105.8 (d, C-2'), 108.3 (d, C-5'), 121.7 (d, C-6'), 123.6 (d, C-7), 130.1 (s, C-1'), 132.9 (d, C-8), 147.8 (s, C-4'), 148.1 (s, C-3'), 166.8 (s, C-2), 172.3 (s, C-4).

The structural formula thereof is shown below.  KAVA-1

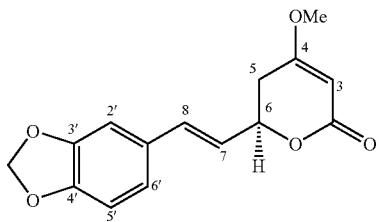

Compound 6 (KAVA-6) (+)-Dihydromethysticin (*Planta Med.*, 64, 504–506, 1998)

The structural formula thereof is shown below.  KAVA-6

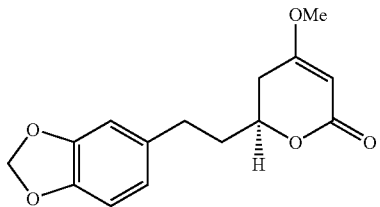

Compound 7 7,8-Epoxyyangonin; (4-Methoxy 6-[2-(4-methoxyphenyl)oxirane]-2H-pyran-2-one)

[α]$D_D^{18}$+13.04° (c1.51,CHCl3) EI-MS: m/z 274 (M$^+$, 5%), 258 (100%), 230 (64%), 187 (66%) HR-MS: m/z 274.0851, C$_{15}$H$_{14}$O$_5$ requires 274.0841 FT-IR (KBr) $v_{max}$ cm$^{-1}$: 2940, 1721 (C=O), 1645 (C=C), 1613, 1566, 1252, (C—O—C), 1181 600 MHz $^1$H NMR (CDCl$_3$): δ 3.69(3H, s, 4'-OMe), 3.77(3H, s, 4-OMe), 5.22(1H, d, J=2.2 Hz, H-3), 5.73(1H, d, J=2.2 Hz, H-5), 6.82(2H, d, J=8.7 Hz, 2', 6'-H), 7.25(2H, d, J=8.7 Hz, 3', 5'-H).

150 MHz $^{13}$C NMR(CDCl$_3$): δ 42.9(d, C-7), 45.5(d, C-8), 55.1(q, 4'-OMe), 55.6(q, 4-OMe), 87.6(d, C-3), 101.2(d, C-5), 113.8(d, C-3' and C-5'), 128.4(d, C-2' and C-6'), 129.4(s, C-1'), 158.5(s, C-4'), 162.9(s, C-6), 164.1(s, C-2), 107.5(s, C-4).

The structural formula thereof is shown below.

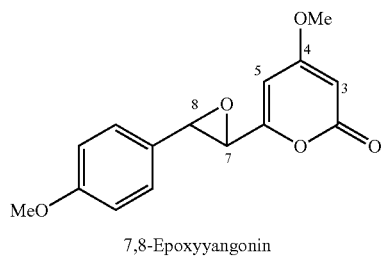

7,8-Epoxyyangonin

Test Examples in relation to the present invention will next be described.

Test Example 1

Inhibition of TNF-α Production (In Vitro)

In response to stimulation by okadaic acid (9,10-deepi-thio-9,10-didehydroacanthifolicin), BALB/3T3 cells produce TNF-α. The compounds of the present invention were investigated in terms of inhibitory effect on TNF-α production.

An MEM medium (product of Nissui) containing 10% fetal calf serum (product of Biocell Laboratory) was injected into 12-well multiplates (product of Corning), and BALB/3T3 cells were disseminated at 2×10$^5$ cells/well. The cells were cultured in a carbon dioxide gas incubator (5% Co$_2$, humidified, 37° C.). Subsequently, KAVA-1, KAVA-2, KAVA-3, KAVA-4, or KAVA-5 was added to the wells at a concentration shown in FIG. 1, and the cells were cultured for one hour. No KAVA compound was added to the control wells. After completion of culturing, okadaic acid (carcinogenisis promoter isolated from *Halichondria okadai*) was added to each well at a final concentration of 0.2 μM, and culturing was performed for 24 hours. After completion of this culturing, the TNF-α concentration of the supernatant of each well was measured by means of ELISA system (product of Genzyme). The results are shown in FIG. 1. In FIG. 1, the amount of TNF-α release corresponding to each compound concentration is represented by a percent concentration based on the amount of TNF-α release measured for the control (100%).

KAVA-3 was found to inhibit TNF-A production to approximately 60% (at 10 μM) the TNF-α production of the control; to approximately 22% (at 50 μM) the TNF-α production of the control; and to approximately 0% (complete inhibition) (at 100 μM). KAVA-2 was found to inhibit TNF-α production to approximately 22% (at 100 μM). KAVA-5 and KAVA-1 exerted similar inhibitory effects; i.e., exerted inhibition to approximately 39% (at 100 μM). KAVA-4 exerted no inhibitory effect at concentrations of 50 μM or less, but exerted inhibition to approximately 60% (at 100 μM). In other words, KAVA-3 and KAVA-2 exerted a strong TNF-A production inhibitory effect, and KAVA-5 exerted a TNF-α inhibitory effect to an extent similar to that of KAVA-1.

Test Example 2

TNF-α Inhibitory Effect (In Vivo)

Male BALB/cAnNCrj mice of 6 weeks age were purchased from Japan Charles River, and those having body weights of 30 g or lower were tested.

Seven mice groups, each group consisting of six mice, were provided; i.e., 1) a group to which distilled water for injection was administered (non-treated group) (N); 2) a group to which a 0.3% carboxymethyl cellulose-Na (0.3% CMC-Na) suspension was administered (control group) (C); and 3) five groups to which KAVA-1, KAVA-2, KAVA-3, KAVA-4, and KAVA-5, respectively, were administered (0.3% CMC-Na was used as a solvent).

Each of KAVA-1, KAVA-2, KAVA-3, KAVA-4, and KAVA-5 was prepared to a drug liquid of 40 mg/10 ml. The liquid was intraperitoneally administered at 10 ml/kg (dose: 40 mg/kg), and 0.3% CMC-Na was intraperitoneally administered at 10 ml/kg to each corresponding group. Lipopolysaccharide (LPS) (product of SIGMA) was dissolved in physiological saline, and the solution was intraperitoneally administered to each mouse in an amount of 0.2 ml (50 µg/mouse) immediately after administration of the drug liquid.

After 90 minutes from administration of LPS, blood was collected from the eye socket, and the collected sample was allowed to stand for one hour at room temperature. Subsequently, the sample was centrifuged at 11,000 rpm for five minutes, and the serum was collected. The TNF-α in the serum was assayed by use of an ELISA kit ([(m)TNFα] mouse ELISA system, product of Amersham Pharmacia Biotech K.K.). The results are shown in FIG. 2.

Figure 2:
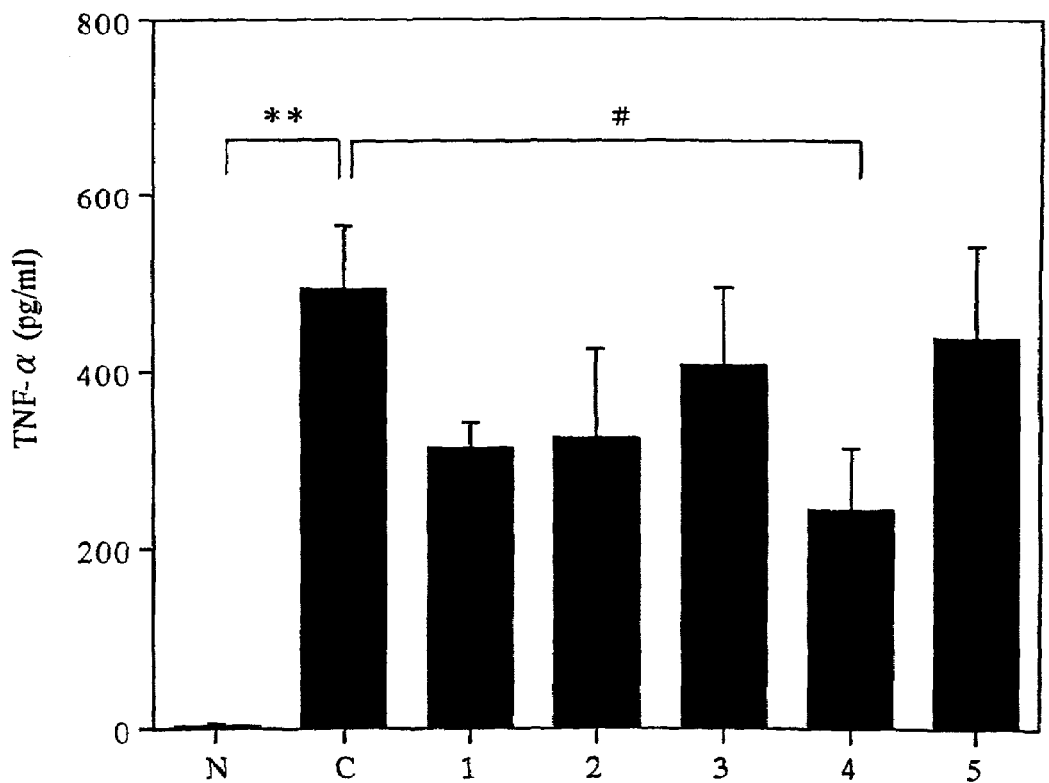
FIG. 2 shows a graph showing investigation results of inhibitory effects of KAVA-1, KAVA-2, KAVA-3, KAVA-4, and KAVA-5 on TNF-α production in serum samples, the TNF-α production having been induced by intraperitoneally administering KAVA-1, KAVA-2, KAVA-3, KAVA-4, and KAVA-5 to BALB/c mice, followed by administration of LPS immediately thereafter.

The results shown in FIG. 2 indicate that KAVA-4 significantly ($p<0.5$) inhibited TNF-α production as compared with the control group (C), and the TNF-α production inhibitory effect exerted by KAVA-1 was almost comparable to that exerted by KAVA-2.

As is clear from the above test results, all kavalactones of the present invention (compounds 1 to 5) can inhibit TNF-α production. The TNF-α production inhibitory effect of compounds 6 and 7 can also be confirmed on the basis of the above test results.

Since the TNF-α production inhibitor of the present invention and the preventive, ameliorating, or therapeutic agent of the present invention for a variety of diseases caused by abnormal production of TNF-α are highly safe and exhibit an excellent effect of inhibiting TNF-α production, the inhibitor and agent are useful as a preventive, ameliorating, or therapeutic agent for mammals, including humans, and for a variety of diseases caused by abnormal production of TNF-α, including cachexia attributed to cancer or infectious diseases, septic shock, chronic rheumatoid arthritis, inflammatory diseases such as ulcerative colitis and Crohn disease, osteoarthritis, Kawasaki's disease, multiple sclerosis, Behchet's disease, systemic lupus erythematosus (SLE), rejection during bone marrow transplantation, multiple organ failure, malaria, AIDS, meningitis, hepatitis, and type-II diabetes.

What is claimed is:

1. A method of inhibiting TNF-α production in a patient in need thereof, comprising administering to the patient an therapeutically effective dose of dihydrokavain, wherein said patient suffers from one or more diseases selected from the group consisting of septic shock, chronic rheumatoid arthritis, ulcerative colitis, crohn disease, osteoarthritis, Kawasaki's disease, multiple sclerosis, Behcet's disease, systemic lupus erythematosus, rejection during bone marrow transplantation, multiple organ failure, malaria, AIDS, meningitis, hepatitis, and type-II diabetes.

2. The method of claim 1, wherein said patient suffers from chronic rheumatoid arthritis.

3. The method of claim 1, further comprising administering at least one additional kavalactone selected from the group consisting of kavain, yangonin, methysticin, dihydromethysticin, and 7,8-epoxyyangonin.

* * * * *